United States Patent [19]
Satake et al.

[11] Patent Number: 5,917,927
[45] Date of Patent: Jun. 29, 1999

[54] GRAIN INSPECTION AND ANALYSIS APPARATUS AND METHOD

[75] Inventors: Satoru Satake, Tokyo, Japan; Rodney S. Baishiki, Belmont; Jeffrey M. Moser, Oakland, both of Calif.

[73] Assignee: Satake Corporation, Tokyo, Japan

[21] Appl. No.: 08/822,771

[22] Filed: Mar. 21, 1997

[51] Int. Cl.$^6$ .................................................... G06K 9/00
[52] U.S. Cl. .......................................... 382/110; 356/237
[58] Field of Search ............................ 382/110; 356/237; 348/89, 91, 129, 130; 209/576, 588

[56] References Cited

U.S. PATENT DOCUMENTS

| | | | |
|---|---|---|---|
| 4,572,666 | 2/1986 | Satake | 356/239 |
| 4,661,985 | 4/1987 | Asuksu | 382/110 |
| 4,687,107 | 8/1987 | Brown et al. | 382/110 |
| 4,713,781 | 12/1987 | Brizgis et al. | 382/110 |
| 4,752,689 | 6/1988 | Satake et al. | 382/110 |
| 4,975,863 | 12/1990 | Sistler et al. | 382/110 |
| 5,135,114 | 8/1992 | Satake et al. | 209/558 |
| 5,321,764 | 6/1994 | Cullen et al. | 382/110 |
| 5,379,949 | 1/1995 | Massen et al. | 382/110 |
| 5,526,437 | 6/1996 | West | 382/110 |
| 5,703,784 | 12/1997 | Pearson | 382/110 |
| 5,703,960 | 12/1997 | Soest | 382/110 |
| 5,710,833 | 1/1998 | Moghaddam et al. | 382/118 |

OTHER PUBLICATIONS

"Satake Broken Rice Analyzer" (Published 1994).

*Primary Examiner*—Jon Chang
*Assistant Examiner*—Jingge Wu
*Attorney, Agent, or Firm*—Flehr Hohbach Test Albritton & Herbert LLP

[57] ABSTRACT

Rice and other grains are inspected by a video camera system, and the data are processed to determined grain measurements, whether each grain is broken, and to obtain measures such as the percent broken by weight of a sample of rice. The apparatus takes a sample of grains or a stream of grains, and conveys it into view of a video camera. The grains in the camera's view are illuminated by an illumination system. After the grain images have been acquired by the camera and electronics, the grains are then removed from the camera's viewing area to an output stream or hopper, and uninspected grains may be conveyed into the camera's view to continue the process. The image data is processed to identify individual grains and then to perform measurements on them.

16 Claims, 5 Drawing Sheets

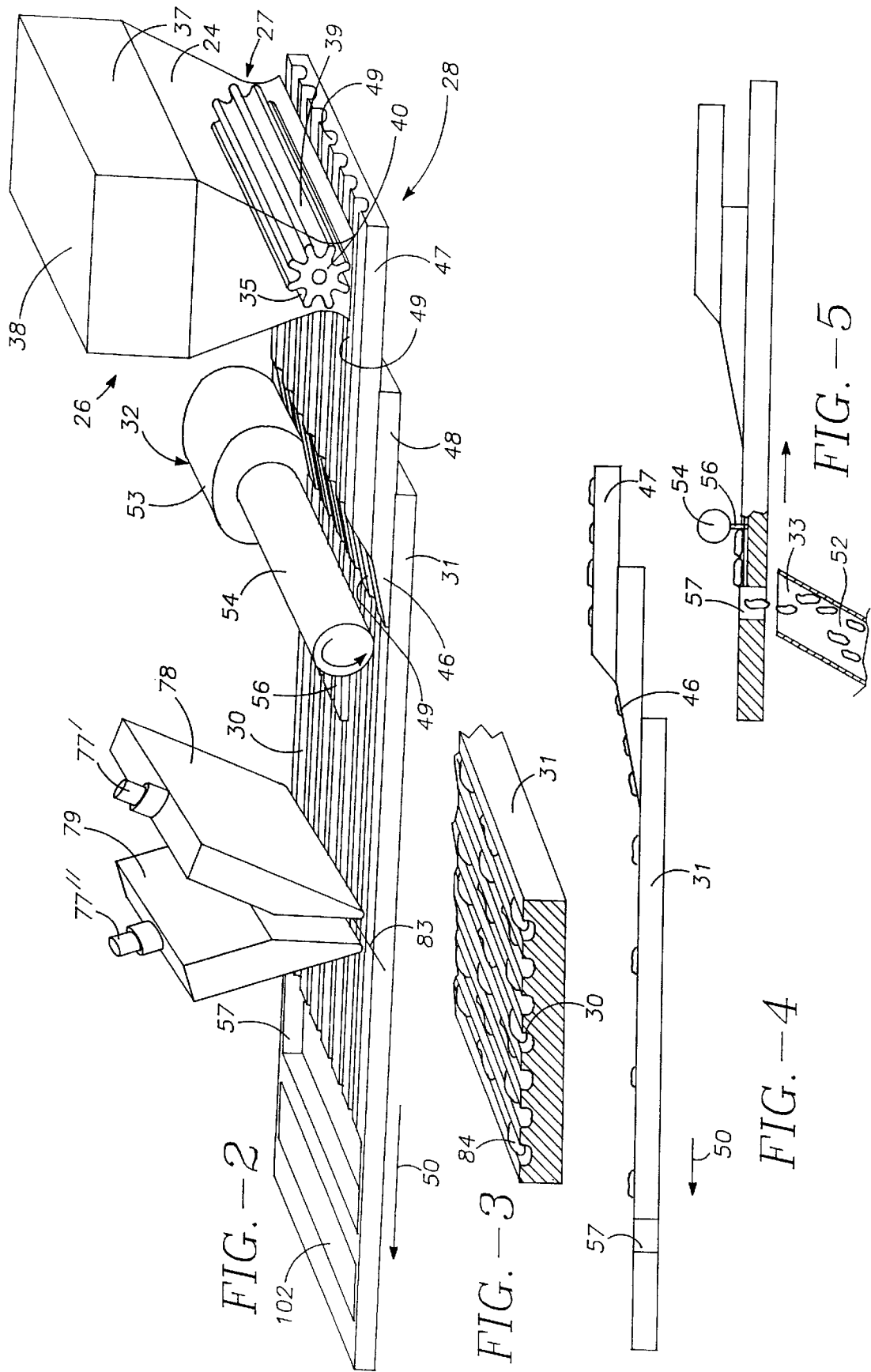

GRAIN INSPECTION AND ANALYSIS APPARATUS AND METHOD

FIELD OF THE INVENTION

This invention relates to the area of automatic inspection systems, and in particular relates to the automatic inspection of rice, other grains, or other products, and the determination of their size and/or broken content.

BACKGROUND OF THE INVENTION

Grain size can be an important factor in rice milling. Size information of individual grains from a population or sample of grain or grains can be useful in determining the variations, distribution, and range of grain size. This can be used for optimization of sieve hole sizes and shapes for size sorting, which can lead to more efficient milling and higher yields and enhanced revenue. Sizing is typically performed by passing the rice grains through a sequence of sieves with different hole sizes and observing the fraction of the sample that remains behind or over each sieve.

The broken content of a sample of rice is a factor in determining the grade of a lot of rice from which the sample was taken, and therefore effects the lot price. The broken content also can be a measure used in the determination of the effectiveness and in the optimization of the rice milling process. Oblong-shaped rice grains, especially medium and long grain types, are susceptible to breakage during the milling and handling process. It is generally desirable to minimize the losses from grain breakage and over-milling, while efficiently yielding a sufficiently-milled product. The amount of broken grains, typically expressed as a percent of the total by weight, is an important factor in optimizing a rice mill.

Presently, the determination of broken content of lots of rice is performed by humans sorting samples of grains, or an approximate determination is made by processing the grains through sieves with specified hole sizes to let the smaller pieces fall through, which would include many of the broken pieces. The sieve method is not very accurate, in part because there can be a significant variation in the size of the whole grains and their shapes. Furthermore, whether an individual grain will pass through the sieve screen is a function of several other significant factors besides the size and the whole/broken classification as specified by a standard.

The manual method of sorting grains is tedious and time consuming, and the results are subject to the subjectivity of humans. The human inspectors are often highly trained and may be subject to testing and certification. Even so, there is generally a significant variation in the determination of broken content between inspectors, and a particular inspector may produce results that are biased or change over time. A less subjective, more consistent, and accurate method is desirable, so that the grading may be more consistent and fair, and so that the milling process may be altered and fine-tuned to optimize it.

Rapid, accurate, and low-cost measurement of broken content can yield advancements in milling optimization and automated process control of a rice mill. This can reduce costs and increase profits. An apparatus configured for online measurements can act as a critical sensor in controlled or automated mills or other plants.

There are various criteria and standards for determining whether a grain is broken. The US Department of Agriculture standard for rice is that the length of a piece of a rice grain must be less than 75% of its original length for it to be classified as broken. Simple length measurement is insufficient because the length of a whole small grain may be less than 75% of a large whole grain, which could result in a large percentage of grains that would have lengths within a range of lengths that are ambiguous as to whether they are broken or not.

Presently there are no automatic inspection systems that are known that can accurately determine whether a grain is considered broken or not, or determine the broken content of a sample. An apparatus that performs the inspection and analysis functions is advantageous to the rice-milling industry in particular, and can also be applied to processing and grading of other grains, seeds, food, and manufactured products.

OBJECTS OF THE INVENTION

An object of the present invention is to provide a method and apparatus for automatically inspecting grains and determining if the individual grains are broken.

Another object of the invention is to provide a method and apparatus for automatically inspecting rice to determining the amount of broken grains, such as in terms of percent of the total by weight. This can provide an automated, more objective, more accurate, more consistent, and faster analysis than human inspectors performing this function.

Yet another object of the invention is to provide a method and apparatus for automatically inspecting rice and provide information that can be used to adjust and/or optimize the rice-milling process and processing plant operations.

Still another object of the invention is to provide a method and apparatus suitable for automatically inspecting samples from the various streams in the milling process to monitor the process and provide information on an ongoing basis.

A further object of this invention is to provide an apparatus that can automatically inspect rice grains and provide size information on the individual grains, and optionally provide compilations of the size data such as the distributions of the various parameters.

And yet another objective of this invention is to provide a method and apparatus that can be used for inspecting other agricultural grains and products.

SUMMARY OF THE INVENTION

The inspection apparatus conveys an input stream of rice grains into the viewing area of a video camera, or other light sensing device, which scans the rice grains and produces image data. The light sensing device measures multiple regions that are each significantly smaller than the grains in order to image them with sufficient spatial resolution to make sufficiently precise distance and area measurements. The grains in view of the sensor are illuminated while they are being sensed. After they have been imaged, they are conveyed to an output stream or bin. A processing system extracts size information from the image data. The processing system or processor uses the image data to obtain information regarding the length, width, and area of the rice, and provides a decision as to the class of each grain, whether they are classified as broken or whole, and determines and provides the broken content of the grains of a sample or stream of rice or other products being inspected. The processing system can compute and/or provide additional information, as desired.

BRIEF DESCRIPTION OF THE DRAWINGS

The invention herein will become apparent from a consideration of the accompanying drawings and ensuing description of which:

FIG. 2 is an enlarged perspective view of the grain handling and conveying system of FIG. 1.

FIG. 3 is an enlarged view of a section of the grain conveyance tray shown with grain.

FIG. 4 is a schematic side elevational view of a portion of the grain handling and conveying system showing grain singulation.

FIG. 5 illustrates removal of grain from the tray.

DESCRIPTION OF PREFERRED EMBODIMENT

Figure 1:
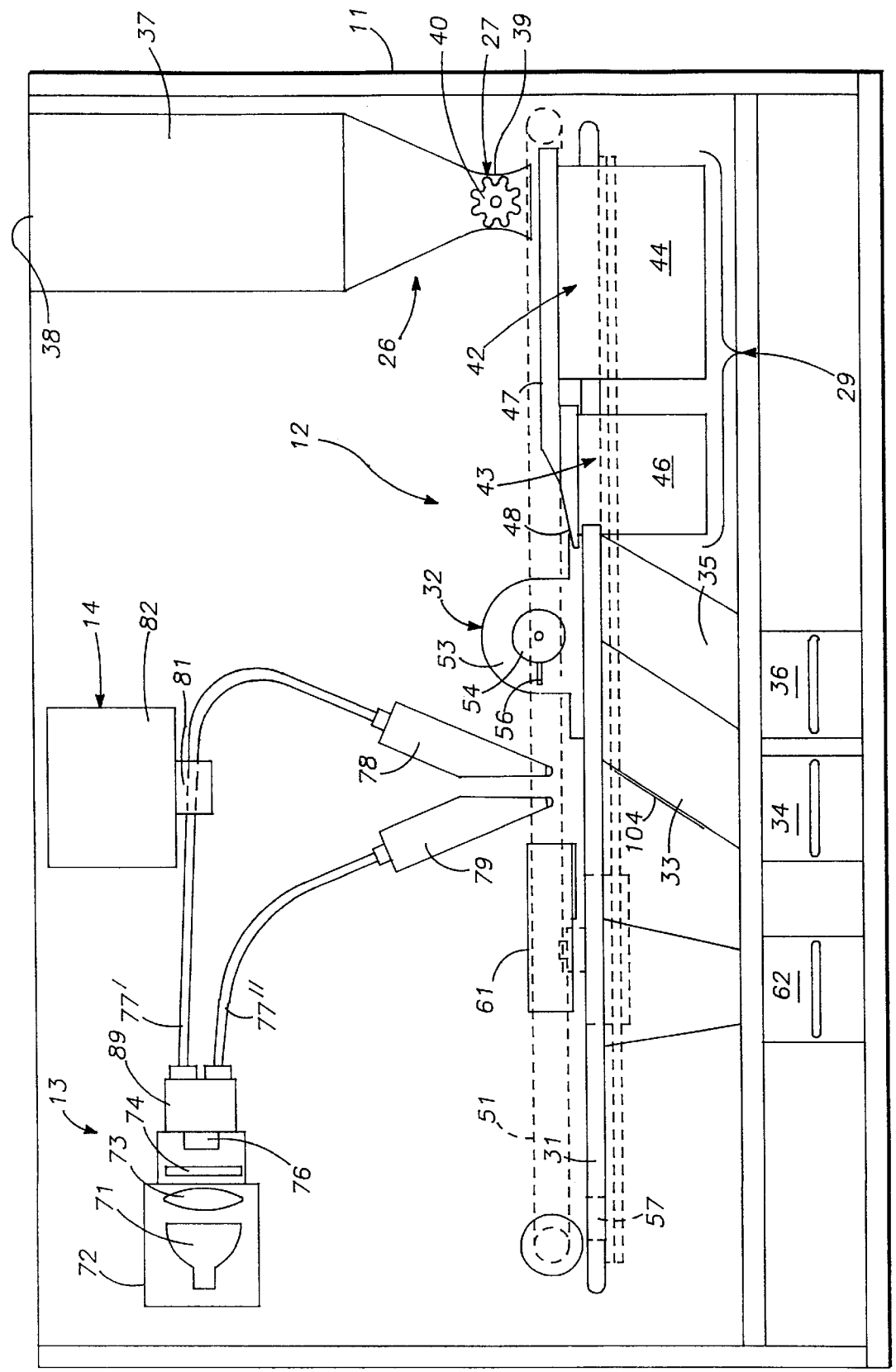
FIG. 1 is a front elevational view of an analyzing and inspection apparatus in accordance with the present invention.

Referring to FIG. 1, the apparatus includes a frame that supports the components that implement grain handling system 12, the illumination system 13 and the light-sensing system 14. Electronic controls, power supplies, drives and other components may be mounted on the frame 11. A signal processor unit 17, FIG. 9 can be mounted on the frame 11 or it may be housed in a separate unit that communicates with the frame-mounted components through a cable or other means.

Figure 9:
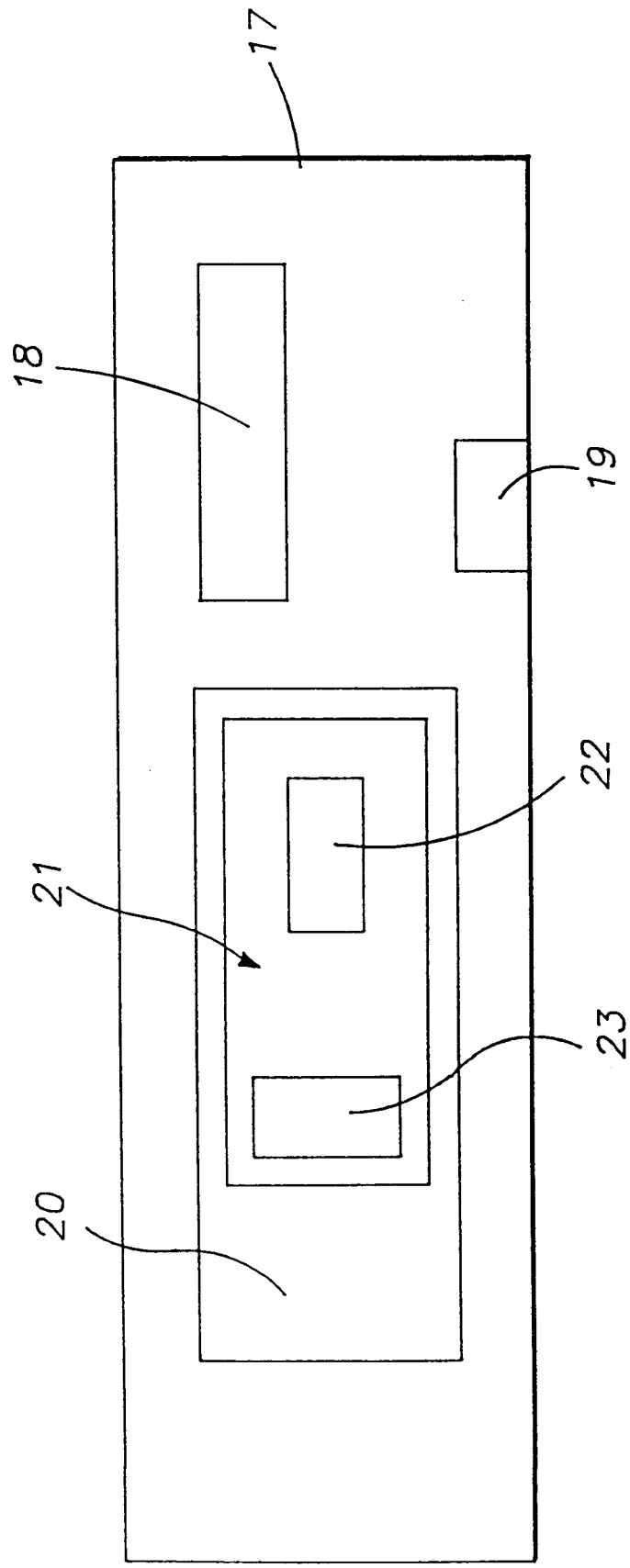
FIG. 9 is a schematic block diagram of the signal processor unit.

The signals from the light sensing system are applied to the processor. The processor includes one or several computer(s) or other computing or processing means that process the applied signals and provides an analysis of the inspected grain. The processor also contains one or several means of displaying or communicating the analysis information to the user or other equipment or systems. FIG. 9 schematically illustrates a processor unit 17 that includes means for displaying and communicating the information, such as a visual display 18, one or more communications ports 19 (such as a serial or parallel data port that may be wires, optical fiber, or wireless), a data processing system 20, including a data processor 21, having an algorithm 22, and a memory device 23 to record the information, and other means as may be appropriate for transferring or relaying the information to the desired place in the desired format. The preferred embodiment utilizes all three of the mentioned information transfer means; the visual display 18 may be a liquid crystal type alphanumeric display mounted on the front panel of the processor unit 17 for viewing by the operator, the port is a standard RS-232 wired serial port, and the data can be stored in the computer's random access, or nonvolatile semiconductor memory devices, or on one or more memory card(s) (containing nonvolatile semiconductor memory devices).

FIGS. 1 through 5 show an apparatus in accordance with the preferred embodiment. Briefly, the apparatus includes mechanical and electromechanical components that convey or handle the grains and presents them individually to the illumination system 13 and the light-sensing system 14.

The grain-handling system 12 includes a grain input hopper 26 or a grain input feed that is supplied with grains for inspection. A metering type feed mechanism 27 provides a regulated flow of grains onto a vibratory conveyance mechanism 29 that acts to singulate the grain and feed the grains in a controlled manner onto a grain-conveyance tray 31. A grain-removal system 32, to be presently described, engages the grain on the tray as the tray moves to discharge the grains into a chute 33. The chute directs the grains to a hopper 34 for storage. Alternately, the grains could be discharged onto or into a grain-output mechanism to transport or transfer the inspected grain to external equipment. Another chute 35 is provided for receiving grains directly from the vibratory conveyance system 29 and delivering the grains to hopper 36, if the user does not want to inspect the grains.

The input hopper 26 includes a storage compartment 37 with an opening 38 for filling the hopper, and a second, lower opening 39, which includes the feed mechanism 27. The feed mechanism 27 comprises a grooved cylinder 40 supported by bearings or bushings (not shown) and driven by a motor (not shown). As the cylinder rotates, a metered quantity of grain is transferred from hopper 26 onto the conveyor mechanism 29. In alternate embodiments the external opening of the input hopper may be located in other positions and may be connected to one or several feeding mechanisms such as a conveyor belt, channel, vibrating feeder apparatus, etc. If one or several such feeding mechanisms are used, the hopper may be eliminated or integrated with such input feeding mechanisms. These other feeding mechanisms may include means to sequentially sample grains from several streams of grain, or to select a particular stream of grains for sampling. Feed mechanism 27 feeds the grains onto the vibratory conveyance mechanism 29, which feeds them onto the tray 31 of the grain-handling system 12. The tray 31 moves the grain into and out of the view of the light-sensing system 14.

The tray 31 moves back and forth laterally under the grain-feeding components of the vibratory feeder mechanism 29. The vibratory feeder mechanism 29 has two independent stages 42 and 43. The first stage 42 of the vibratory feeder mechanism is fed grains from the feed mechanism 27 and in turn moves the grain onto the inclined surface of the second stage 43 of the vibratory feeder mechanism. Stage one and two each include a vibrating drive 44 and 46, and a top plate 47 and 48, respectively. The top plates each have one or several channels, troughs, or grooves 49, shown in FIG. 2, in their upper surfaces that are aligned substantially parallel with each other. One end of the second-stage top plate 48 extends under and in close proximity to the discharge end of the first-stage top plate 47 to receive the grains discharged by the first stage. In the second-stage top plate 48, troughs extend down an inclined surface in alignment with the grooves or troughs 49 in the first-stage top plate 47 and the grooves or troughs 30 in the tray 31. By way of illustration, seven troughs are shown in the top plate 47 and 48 and tray 31; however, any reasonable number of troughs may be used. The shapes of the troughs 49 in the plates 47 and 48 are preferably designed to be conducive to transporting the grains at a reasonable speed and conducive to singulation and alignment of the grains in the troughs as the grains are being transported and before the grains are fed onto the troughs 30 in tray 31, which hold the grains in a stable position, so that as the tray moves, the grains are moved into and out of the field of view of the light-sensing system 14. The grains singulate on the top plate 47 and further singulate as they travel down the inclined surface on plate 48. The vibration of the top plates 47 and 48 is provided by the motion in the direction of troughs by the vibrating drivers 44 and 46, which move the top plates 47 and 48 in the direction of the troughs. The characteristics of the vibration, such as frequency and amplitude are selected for enhanced grain singulation and transport rate.

A motor-driven belt, shown as dotted line 51, FIG. 1, drives tray 31 on linear bearings (not shown). The tray is moved back and forth under the top plate 48 to receive grains from the top plate and further singulate the grain. The grain supported by troughs 30 is illustrated schematically in FIGS. 3 and 4. The grain is moved or transported into view of the light-sensing system 14 by movement of the tray in the direction of arrow 50. Electronic control circuitry controls the belt driver to control the speed and direction of the tray 31. After the grain on the tray 31 is viewed by the light-sensing system, the tray is moved in the opposite direction and the grains are removed to commence another scanning cycle. A damper device (not shown) is used at one end of the tray's range of travel, and electronic control circuitry that drives the tray controls the travel and dampening at the other end of the tray's range of travel. Other types of conveyance mechanisms could be employed to present the grain to the viewing area. One such mechanism could have the grains fall off the end of a conveyor so that the grains are individually viewed while they fall.

A grain-removal assembly 32 is mounted to the frame 11 just above the tray and outside the viewing region of the camera near the end of the tray that is fed by the vibratory feeder assembly 29. The grain-removal assembly or sweeper 32 includes a motor 53 and drive system (not shown) that rotates a sweeper 54, which spans the width of the tray. The sweeper includes a number of finger-like protrusions or fingers 56 corresponding to the number and lateral positioning of the grooves or troughs 30 in the tray 31. The sweeper is rotated by the motor 53 to one of two positions. In one position, the fingers are horizontally oriented and sufficiently away from the tray to allow the grains on the underlying tray to pass unimpaired. The sweeper can then be rotated to the discharge or sweep position, where the fingers are vertically oriented and protrude into the underlying troughs 30 of the tray without contacting it, thereby impeding movement of the grain as the tray moves in the direction of the feeder assembly 29. An opening or hole 57 is in the tray 31 at a position near the end of the tray that is furthest from the vibratory feeder. It is preferable that the hole is as small as possible so as to not significantly reduce the length of the tray usable for grain support, but sufficiently large to allow the grains to fall through when they are being swept off the tray by the sweeper. The sweeper is rotated to the vertical position with the fingers extending downward into the troughs when the tray has completed its forward movement and all the grains on it have been viewed by the camera. The grains are then swept off the tray through the hole 57 as the tray moves in its reverse direction, as portrayed in FIG. 5. The chute 33 allows the grains to fall through the hole 57 in the tray 31 into a container 34 that is positioned under the chute 33. Other embodiments may have different arrangements to perform the grain removal function, such as having the grains swept off an end of the tray or pneumatically removed.

A second chute 35 is positioned under the end of the second-stage top plate 48 to receive grain when the tray has traveled out of the way from under the top plate 48. The chute 35 directs the grain into the underlying hopper or bin 36. This arrangement permits grain to be dumped into the bin 36 when there is no need to inspect the grain being fed by the top plates 47 and 48, and also catches grains that may fall off the end of top plate 48 when the tray 31 is not positioned under the end of the top plate 48 that feeds grains onto tray 31.

In order to reduce the errors or inaccuracies that may occur due to the collection of dust, debris, or other substances on the tray 31 or other conveyance means that is viewed by the camera, and to reduce the maintenance time and to increase the maintenance intervals, a tray cleaning system 61 is included in the preferred embodiment. Many different types of cleaning methods and systems could be employed, including systems that use combinations of methods. Examples of methods include stationary brushes, oscillating brushes, rotary brushes, air jets or air curtains, vacuum, and so on. The preferred embodiment uses a vacuum system which collects and deposits the debris and dust into a bin 62. A brush may be included in the sweeper 32. Other embodiments may dispose of the dust and debris in other ways, such as transporting them out of the apparatus and possibly into a waste disposal bin or system. In another embodiment the dust and debris may also be deposited into a bag or other container, such as a filter bag similar to those used in vacuum cleaners.

The illumination system 13 and the light-sensing system 14 form part of a machine vision system. These critical parts of the machine vision system need to maintain optical alignment with the region of the tray illuminated by the illumination system and viewed by the light-sensing system. They are substantially rigidly mounted on the rigid frame 11. This maintains optical alignment between the components, and mitigates the effects of mechanical shock and vibrations that could change the alignment either temporarily or permanently.

The grains are illuminated while they are in the field of view of the light-sensing system 14 by the illumination system 13. Referring to FIGS. 1 and 2, the illumination system is above the tray and illuminates the grains and tray. The reflected light is sensed by the light-sensing system 14.

The illumination system may, for example, as used in the preferred embodiment, include a tungsten-halogen reflectorized light bulb 71 mounted in a housing 72 that isolates the light bulb from the surroundings and holds the bulb in position. Light travels through a plano-concave lens 73, which focuses the light through a infrared-blocking optical filter 74 for highly attenuating portions of the infrared spectrum that can generate heat but to which the camera in the light-sensing system 14 is substantially insensitive. The light is directed into the ends of a bifurcated fiber-optic bundle 76. The light travels through each arm of the bundle 76 to light manifolds 78 and 79 at the end of arms 77' and 77", respectively. Each manifold holds the optical fibers at the end of each bundle in a line that is perpendicular to the direction of travel of the tray 31 and parallel to the plane of the tray at a constant height above the tray. The manifold holds the ends of the fibers in the bundles in a position to concentrate illumination into the field of view of lens 81 of the light-sensing system 14. The illumination is substantially a line segment extending across the top surface of the tray perpendicular to the direction of the tray's travel. The two manifolds are positioned on either side of the field of view of the light-sensing system 14 so as to substantially evenly illuminate the grains as they pass through the field of view. In order to diffuse the light transmitted to the tray and grains to provide substantially uniform lighting (less spatial variations of light intensity) across the tray in the viewing region, the output ends of the fibers may be processed to have a light-diffusing transmissive surface, or light-diffusing glass as in the preferred embodiment, or other translucent material can be located at the light output ends of the fibers. Various other illumination arrangements could be employed to uniformly illuminate the grains in the field of view.

Figure 6:
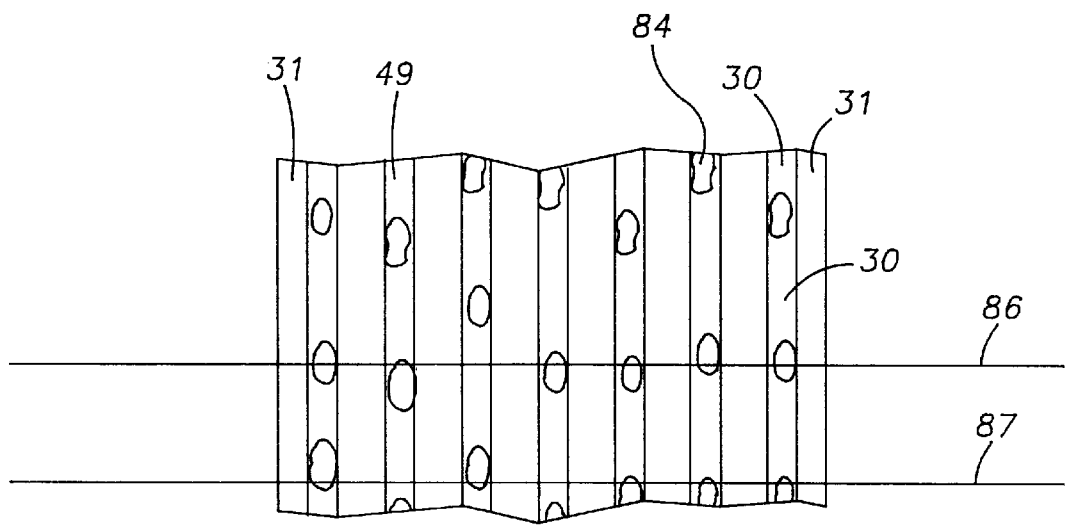
FIG. 6 is a top plan view of a portion of the grain conveyance tray.
Figure 7A:
FIGS. 7A and 7B show the analog output signal from a line-scan light sensor source as it views the grains along the lines 86 and 87 of FIG. 6.
Figure 7B:
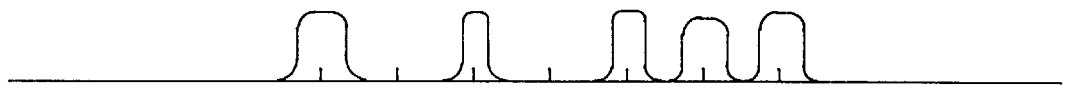

Lens 81 of the light-sensing system 14 directs light into a line-scan camera 82, which detects light reflected by the grains and tray. The line-scan camera 82 is focused along a line 83, FIG. 2, between the light manifolds 78 and 79, on the surface of the tray. The camera includes a semiconductor pixelated light sensor such as a line-scan charge-coupled device or similar array of light-sensitive elements. Light reflected from the tray and grain is sensed by the in-line pixelated sensors. The outputs from the pixelated sensors are sequentially and repetitively scanned to obtain and extract the boundary of the image of each inspected grain by detection of the intensity of light received by the sensors. Referring to FIG. 6, the grains 84 on the tray 31 are shown at one moment in time during which the tray travels in the forward direction. By way of illustration, as the tray moves, lines 86 and 87 are scanned at different times. These lines correspond to fields of view of the camera acquired at different times while the tray is traveling in the forward direction. The analog video output signals from the line-scan camera at lines 86 and 87 are shown in FIGS. 7A and 7B, respectively. The scanning is synchronized with the tray movement, whereby in the preferred embodiment, there were about 12 scans per millimeter of travel of the tray. The spatial resolution is improved by increasing the number of scans for each millimeter of movement. The length corresponds to the number of pixels in the lengthwise direction of the grain. In the preferred embodiment, this corresponds to the direction of the tray movement, in which the transport system attempts to orient the grains lengthwise. This direction is substantially perpendicular to the scan lines, exemplified by scan lines 86 and 87, measured by the line-scan camera. The length of a grain can be computed as the number of pixels in a particular line perpendicular to the scanned lines that contains the most pixels within the grain boundaries. The length of a grain can also be computed as the number of pixels in a line perpendicular to the scan lines that contain a pixel within the boundaries at each end of each grain, which is the method implemented in the preferred embodiment. Alternate embodiments can have computations of the major axis of the grain and the length computed based on this axis rather than the line parallel to the tray travel. The length can be computed as the length of this major axis within the grain boundary, the length of a line within the grain boundary parallel to the major axis, or the distance between two lines that are tangent to the grain boundary at its ends that are perpendicular to the major axis. The width of a grain can be computed as the number of pixels from the maximum to the minimum pixel number within the grain boundary along the scanned lines that intersect the grain boundary. These scanned lines are, in the preferred embodiment, substantially along the width of the grain due to the orientation of the grain with respect to the camera. The width can also be computed as the maximum number of pixels within the grain boundaries along a particular scan line, as is the case for the preferred embodiment. Alternate embodiments can have computations of the minor axis of the grain and the width computed based on this axis rather than a scan line. The width can be computed as the width of this minor axis within the grain boundary, the length of a line within the grain boundary parallel to the minor axis, or the distance between two lines that are tangent to the grain boundary at its side that are perpendicular to the minor axis. In the preferred embodiment, the area of each grain is computed as the number of pixels within the grain boundary.

Figure 8:
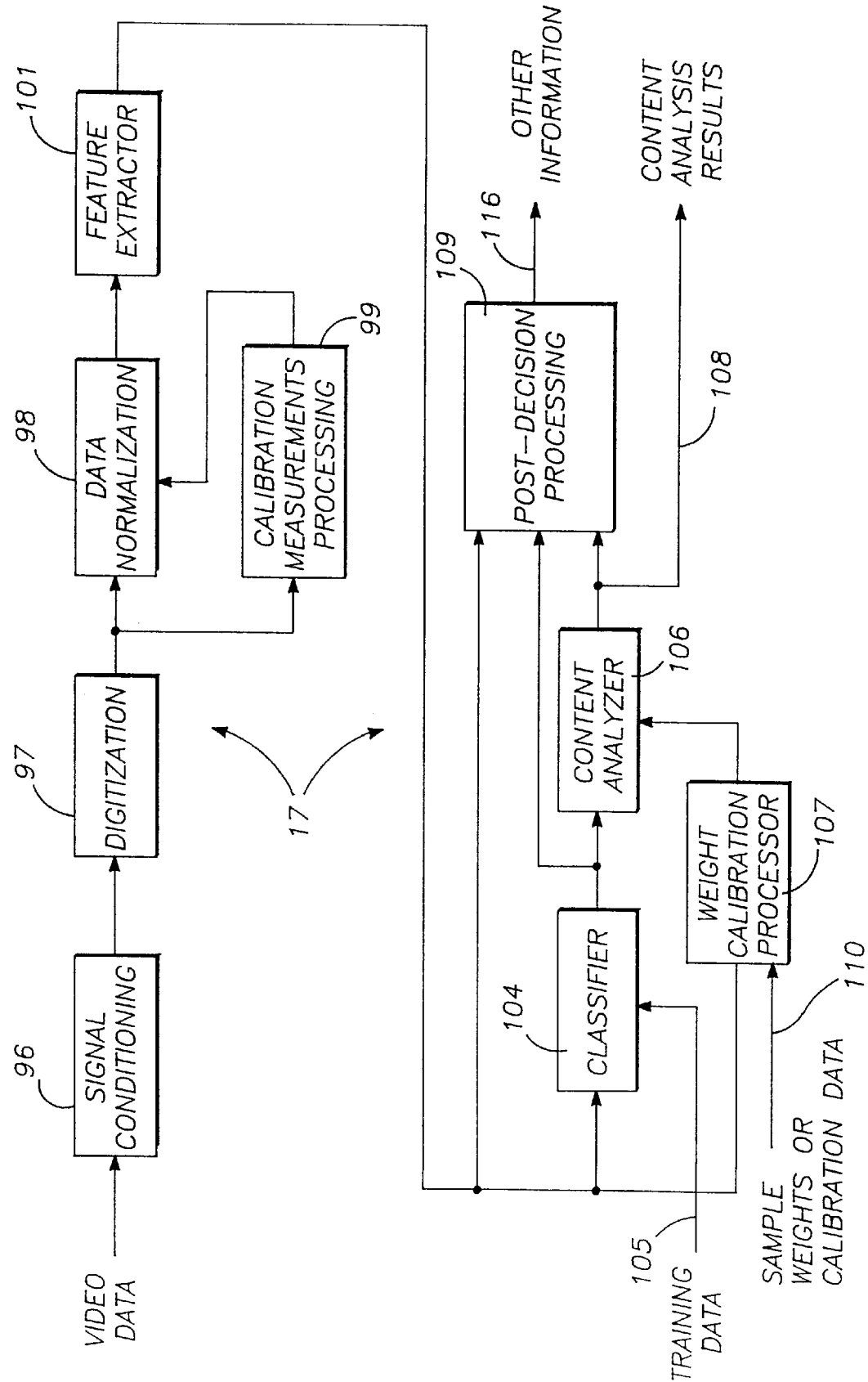
FIG. 8 is a block diagram of the signal processing electronics.

FIG. 8 portrays the basic signal processing that is implemented in electronic circuitry and software in the processor unit 17, shown in FIG. 9. The video analog signals from the camera 82 are conditioned by signal conditioner 96. A digitizer 97 digitizes the analog signals. A data normalizer 98, which is responsive to calibration signals from a calibration circuit 99, can be implemented in analog and/or digital circuitry. Other embodiments may use different processing steps and/or modify or eliminate one or several steps. The preferred embodiment uses such processing as digital data normalization to yield high-accuracy results that change minimally over time and with component-to-component variations, and also for equalizing pixel response, which may vary across the field of view due to spatial variations in illumination and variations of pixel responses of the camera.

The preferred embodiment also has the capability to perform initial and updated calibration measurements to provide the calibration factors used by the normalizer 98 to compensate for baseline variations of light level that may exist across the viewing area and/or may vary over time, and to compensate for variations in sensitivities and offsets of the pixels of the camera and video signal. Other embodiments may include more or less amounts of calibration and normalization processing, and may possibly have none at all. The computer controls the timing of the calibration processing so that the data acquired from the camera when the calibration standards, to be described, are in its view. The calibration data are used for computing the calibration factors, and not used as grain image data.

The system is calibrated for high and low light levels. A white calibration region or high-light-level calibration standard 102, shown in FIG. 2, at the end of the tray 31 provides calibration of high light levels. This region has a reflective surface that has substantially uniform reflectivity. It may be any shade of gray or white, or even a color, but is preferably white or a shade of gray with a reflectivity that yields light levels that are near the upper part of the dynamic range of the light responsivity of units by applying the appropriate dimensional calibration factors.

One method to extract the features is to extract the boundary of the image of the inspected grain and then extract the measurements from this data. All pixels that have a light intensity value at or above a specified threshold value are considered to be within the grain boundaries, and the pixels with values below the threshold value are considered to be outside the boundaries of the grains. These boundaries can be used to define each grain. The feature information for each grain is then processed to classify each grain. Other embodiments may include processing of the data that detects when grains are touching each other, and accounts for or defines the grain boundaries that may be missing in the data. Other embodiments may include processing of the data that accounts for and/or corrects misalignment of the grains in the troughs of the tray or other presentation means that may not have capabilities to consistently orient the grains for viewing by the camera. The preferred embodiment utilizes a fairly refined grain conveyance system that minimizes the amount of grains touching each other on the tray and maintains a sufficient degree of consistent grain alignment of the longer axis of a grain parallel to the direction of travel of the tray.

The extracted features are first processed by classifier 104, which classifies each grain. The grains are classified by comparing the extracted feature information with information contained in a look-up table. In the preferred embodiment, the classifier makes decisions from the grain feature data as to whether each grain is broken or not. In alternate embodiments, the data from the broken grains could be further processed by the classifier, or processed by a classifier that makes a three-way or greater classification, rather than the two-way classification as in the preferred embodiment, to determine one or several classes or categories of broken grains. A three-way the light-sensing system and data-processing system. In the preferred embodiment, this high-light-level calibration standard is a calibration plate that is white and has reflective properties of diffuse reflectivity with low specular reflective content. The preferred embodiment also uses a low-light-level calibration standard. This is substantially black or devoid of light in the camera's field of view. In the preferred embodiment, it is implemented by the hole 57 in the end of tray 31. The hole acts as a black standard because the camera lens is adjusted to focus on a line at the tray, and the field of view diverges in the region below the hole and is out of focus. The illumination also diverges and has greatly diminished luminance at the surfaces below the tray. The greater distance also diminishes the light reaching the camera. In order to further reduce the light received by the camera, the preferred embodiment uses a black diffusive surface 104, which is mounted on the chute 33 in the field of view of the camera below the hole 57. The high-level and low-level calibrations may be obtained when the respective calibration standards are in the field of view of the camera, which can occur during each tray-movement cycle. Another embodiment can use a mechanism that moves one or several calibration standards having either high- or low-light level, or both, into and out of the field of view of the camera. The calibration standard can be moved into view periodically for calibration, such as before each run, and possibly before each tray-movement cycle.

The normalized data is processed by the feature extractor 101 to extract features or measurements of length, width, and area, and possibly other measurements, for each grain. In the preferred embodiment, the extractor uses electronic circuitry (hardware) to extract some of the basic information on each grain, and uses a computer to extract other information to compute the measurements, and compile the results. The dimensional measurements can be in arbitrary units, or can be converted to actual dimensional classification addresses standards in some other countries, or could address specific criteria specified by the mill or user. Any number and type of criteria defining the categories of grain could be specified, such as classes that also have area and/or width criteria. Some embodiments may use classifiers that classify the lengths into many classes, such as classes segmented in 1 percent or 5 percent increments. Criteria can also include data not normally computed by the apparatus of this invention, or that was computed or derived by additional functionality included in the apparatus.

The classifications of the grains may be accomplished by several means. The decisions for each combination of feature values are determined by comparisons with values that are previously determined by a training process. The known feature values used for the training process are derived from simulated grain data or actual grain data, which can be acquired by the same or similar inspection system. The classification decisions are arrived at by the classifier 104 using a look-up table (LUT), that is addressed by the combination of the feature values measured by the apparatus. The output of the LUT is a value that either represents the decision, or is a value that is thresholded to produce the decision. For the latter, the threshold may be adjusted to fine tune, modify, or bias the decisions. Feature combinations that lie outside the boundaries of the LUT can have decision based on the value of just one of the features, which allows for a smaller LUT and therefore result in smaller memory requirements. The training process can determine the extent of the LUT and define these decision criteria. These criteria are imparted to the classifier as threshold values for each of the features. These threshold decisions could be determined by the classifier before the LUT is accessed. For any combination of feature values for each grain, a decision is determined by the classifier. Another means to impart the decisions to the apparatus is by mathematical formulas. A parametric method can be used to produce one or several equations or an arithmetic and/or logical algorithm. These are imparted to the classifier. The classifier computes a decision from the grain feature data using the equation(s) and/or algorithm(s). The decision data can be determined by the training process using data from actual samples with known classifications and/or by using simulated data. Algorithms based on methods such as statistical pattern recognition, syntactic pattern recognition, neural networks or other adaptive learning networks or algorithms, genetic, fuzzy logic or sets, and/or other methods or combinations of methods can be used for the training processing. Other signal and data processing can also be used in the algorithms.

The training process can be performed inside the apparatus as a function that is separate from the normal functioning or operation of the apparatus, or can be performed external to the apparatus. In the preferred embodiment, the training process is performed external to the apparatus and is not part of it. Training algorithms based on statistical-pattern-recognition techniques, such as maximum-likelihood classifiers and probability-density estimation, have been used successfully. The preferred embodiment incorporates the results of the training process that uses actual grain data.

If the training process is performed external to the apparatus, the data developed by the training process or training data 105 can be transferred to the apparatus by various means. In the preferred embodiment, the training data that results from the external training process is written onto a memory card, which is a small card containing semiconductor (or possibly other type(s) of) memory, and which is readily interchanged between copies of the apparatus. Other embodiments may use other means to transfer the data, such as by modem or port transfer using wired or wireless communication, either electrical or optical, or by other means ordinary telephone lines can be used for communication.

There are also other means to compute a decision that will become apparent to those skilled in the art. An example is to have a self-training, self-tuning, or adaptive algorithm to train and/or modify the decisions the apparatus makes. These algorithms may be included as part of the apparatus, or could be implemented separately and the data transferred to and from the apparatus.

The decisions made, as to the grains being broken or not or in which class they belong, may be used in various ways. The processor can determine the number of whole and broken grains, and could further determine the number of grains in the various broken categories. Furthermore, the various feature data can be determined for the various categories. In the preferred embodiment, the algorithm determines the traditionally-defined broken content by processing the decisions in the content analyzer 106. The ratio of broken weight to sample weight, referred to as the percent broken by weight, can be computed using the weight of the broken grains and nonbroken grains (whole grains), as is done in the preferred embodiment. The algorithm in other embodiments may simply compute the number and/or ratio (or percentage) of broken and whole pieces, or the number of pieces in each class. The algorithm in other embodiments may compute a histogram or a distribution of the number of pieces in the classes.

The weights of the broken grains and whole grains or total grains may be measured or computed by various means. One method to obtain the weights is to physically separate the grains into groups and/or streams of broken and whole pieces, and then weigh each separated stream, either as groups or individual grains, from a sample or stream for each class of separated product. Instead of separating the grains into separate groups or streams, another embodiment may alternately individually weigh each grain, and these weights and the class decisions are used in the compilation of the total weights in each class. This weighing can be accomplished by various means, such as a load cell or other type of batch weighing system, or a weighing system that continuously or intermittently measures the stream of grains. The weighing system is in communication with the processor so that the processor may acquire the weight data.

One means to obtain the weights is to estimate the weight of each individual grain or piece of grain. This may also be accomplished by estimating the weight using the measured data of each inspected grain. The weight calibration that relates the measured data to the weight can be accomplished by such computational methods as fitting the weight and measured data to a curve or hypersurface (including lines and planes and hyperplanes). The preferred embodiment uses an algorithm that estimates the individual grain weights using the area data of actual grains and their weights to determine a curve that maps the area values into weight values, using the criterion in this case of the least mean-square error. Other criterion or criteria could be alternatively used. The weight calibration can be made by using individual grain data or by using the weight and total area of sample groups of grains. In the preferred embodiment, sufficient accuracy for determining the percent broken content by weight (which is essentially a ratio of weights) was obtained from two samples of grains, one of broken grains and the other of whole grains. The actual measured weights and the areas were used to fit a nonlinear curve or mapping from the grain area to its weight. The area data was raised to the 1.5 power, and this data and the weight data were fit to a second-order polynomial curve using a least-mean-square criterion for goodness of fit. Various algorithms could be used to perform the fit mathematically. The computations can either be performed on external computing devices and the results communicated to the apparatus, or computed and stored within the apparatus. In the preferred embodiment, the weight calibrations can either be computed in the apparatus in weight calibration processor 107 or transferred to it. The content analyzer 106 uses the externally-supplied sample weights or calibration data 110 for estimating the weights of the individual grains inspected. The weight calibration data are weights of individual grains or groups of grains, depending on the weight calibration algorithm used, that are supplied externally. From these estimated weights of grains computed in the content analyzer 106 that have been classified as broken or not, the content analyzer then determines the content analysis results 108 in terms of percent broken by weight and/or in other selected terms.

A LUT can be alternatively used in other embodiments to determine the weight for each grain by predetermining or precomputing the weights for each value of area and loading these into the LUT. In this implementation, the processor accesses the weight data in the LUT by providing a memory address based on a measured area, and the output of the LUT is the weight corresponding to this area. Interpolation can be used to obtain a more precise value from several entries in the LUT corresponding to area values that are close to the measured area value.

Another means for the processor to compute the weights of the individual grains is to use a LUT as described above, and to load it with weights that were obtained by means such as statistical processing of samples. A sample of grains is measured to obtain the individual grain weights and inspected areas. A value for each LUT entry is computed based on the processing of the sample data. A means of obtaining the LUT entries is to compute the averages for each area value and load these into the LUT at the addresses corresponding to the area. The LUT values can be modified further by smoothing the values in the LUT such that they are a weighted average or some other function of the LUT entry and the entries of neighboring area values that are close in terms of area to the LUT entry being computed. This smoothing function can be implemented by other means. Other embodiments can use other methods to compute the LUT entries.

The decisions, features, weight estimates and content results can be compiled and processed to yield information that can be accessed upon request. This processing is performed in the post-decision processor 109 to yield this other information 116.

An embodiment of the invention uses the apparatus to provide data on an ongoing basis. Data that is supplied by the apparatus can be communicated to and used in a process control system. This embodiment includes a communication link with the process control system so that the system can control the apparatus and data can be provided to the system. In this configuration, certain characteristics, parameters, process configuration, and/or other factors of the process can be modified in response to the data supplied by the apparatus. The control system could also use other data besides that supplied by the apparatus of this invention it its algorithm(s) that compute(s) the degree or nature of the control. The process-control system can be automated so that human intervention is normally not necessary. The apparatus can be integrated with or within other part(s) of the control system.

The data from the apparatus of this invention could be supplied or communicated to a data collection and analysis system. Statistical analysis of the process and trend determination could be accomplished using this system. The apparatus could receive and process samples from various locations in the mill or plant. The input to the apparatus could be multiplexed so that the apparatus can be supplied with the samples from the various processing locations or streams, and the input sample could be selected manually or automatically. In this manner or similar manner, the apparatus can be utilized throughout or in several parts of the process or plant, or utilized in several process lines or plants.

The apparatus may be configured to measure samples or discrete entities of grains from one or various processing location(s). Some embodiments may have the apparatus incorporated in the grain-processing line. In a rice mill, for example, the apparatus is supplied by sample streams or sample batches of rice from one stream of rice or one of several streams of rice. Grain-transport means such as chutes, pipes, mechanical conveyors, pneumatic conveyors, etc. connect the streams to the apparatus. A mechanism for sampling the stream would typically be included to yield a flow that corresponds to the throughput of the apparatus. A stream selector mechanism can be included to select the sample stream to the apparatus from several streams. A control system may be included to actively regulate the flow to the apparatus. One example of a simple control system uses a sensor to measure when the grains have filled the input hopper to a predetermined height. The system controls a valve or similar device that slows or shuts off the flow to the apparatus. The grains that have been inspected by the apparatus can be conveyed back to the original stream from where they originated, conveyed to a separate stream, conveyed to a waste stream, held in a hopper that is replaced or emptied periodically, or can be handled in another manner. The data from the apparatus could be manually accessed, or more typically the apparatus would be in communication with the process-control system of the plant. The data would be transferred to the process-control system and the apparatus could be controlled, monitored, and additional information retrieved from it by the process-control system.

Another embodiment may supply a continuous stream of grains to the apparatus, and the apparatus could continuously, periodically, or upon demand, update and supply information. The apparatus may be designed to function in multiple modes, such as being supplied samples on an intermittent, sequential, and/or continuous basis. The apparatus could be configured to accept multiple samples, either sequentially or simultaneously. In an embodiment that has a capability of feeding several different samples simultaneous, individual lanes or troughs throughout the grain conveyance system that are aligned can be fed with grains from different samples supplied simultaneously. In these alternate embodiments, the grain feed system could have multiple feed systems or a segmented feed system that feeds each sample to a separate lane or group of lanes. The processor would have the capability to know which samples are in each lane, and collect the data and compute the results for each sample separately, although possibly performed essentially simultaneously. The apparatus could be configured to analyze samples fed to it either manually or automatically. The apparatus could be used in various other configurations.

Other embodiments may include either in or with the apparatus other capabilities or functionality that allow it to also perform other functions in addition to the broken-grain analysis and/or grain-data measurement. The operator may select which function or functions the apparatus is to perform or the apparatus can perform all functions when testing samples. The apparatus can be configured to perform multiple functions simultaneously and/or sequentially. An example of an embodiment of this apparatus that performs multiple functions and would be particularly useful in rice mills is one that also performs degree-of-milling measurements.

Operation of Invention

In the preferred embodiment that uses the apparatus to perform individual sample analyses, an operator would put into hopper 26 a sample of grains for analysis. The size of the sample may vary, but a larger sample would typically yield a more accurate assessment. A typical size of a rice sample may be 25 to 50 grams. A sufficiently-large hopper could hold even larger samples. A sample feeding mechanism that held multiple samples could be included either in or on the apparatus to facilitate automatic analysis of several samples. With this multiple-sample feeder, the operator could load several samples at one time for analysis, and the apparatus would process them sequentially, or possibly simultaneously.

The operator would set certain parameters that may be required to properly analyze a sample or samples. In the preferred embodiment, training is performed for each different class of rice to develop the decision data supplied to the LUT to analyze various types of rice, such as long grain, medium grain, and other types such as short grain, if desired. The operator may change the apparatus's setting that selects the type of rice to be analyzed. Another embodiment can have the capability embedded in the apparatus to automatically determine the type of rice from the measured data, and perform the appropriate computations using the training data results for the rice type being analyzed. In the preferred embodiment, the operator may also select various parameters that tend to optimize the grain-feeding characteristics to better convey the grains. The general degree of amount broken can be selected to modify the feed characteristics. In the preferred embodiment, there are two general levels of broken content to select, normal (mostly whole grains) and mostly broken, that select different settings of the grain-handling system.

The preferred embodiment also includes other functions that can be selected. An operator may also select particular data to obtain or view, and/or to be collected for further analysis and/or communication to external devices. Other functions to be performed by the apparatus can be also selected, such as cleaning the tray, discharging the grains without inspection, and several apparatus setup, calibration, test, and diagnostic functions.

The operator initiates the apparatus to perform the sample analysis. This is accomplished in the preferred embodiment by pushing a start switch, by command from a computer or terminal in communication with the apparatus, or by command from an automated system in communication with the apparatus. In the preferred embodiment, the apparatus then performs the appropriate calibrations and conveys the grains into and out of view of the light-sensing system 14. The initial calibration at the beginning of each run of a sample is performed by the machine vision system first acquiring data from the low-light-level or black calibration standard. This standard is implemented by bringing hole 57 at the end of the tray 31 under the light sensing system 14, or the tray could be initially moved out of the viewing area. A black diffuse surface 104 under the tray's plane of movement and in the field of view of the camera enhances the low-light level. Data is also acquired from the high-light-level calibration standard or surface 102. Data is acquired, typically several scans (such as 256), and calibration values are computed for each pixel. In the preferred embodiment, the tray moves forward as successive scans of the high-light-level calibration standard are acquired, so as to view different areas on the calibration standard so to average out and therefore reduce the effect of variations in reflectivity across the surface of the calibration standard. The preferred embodiment computes offset and effective sensitivity values for each pixel, and then computes the appropriate normalization values for offset and effective sensitivity of the pixels that will be used in subsequent data processing to substantially equalize the offsets and effective sensitivities of the pixels relative to each other, and to keep them substantially constant over time. The sensitivity normalization substantially accounts for and corrects variations in the light levels in the field of view of and sensitivities of the pixels in the sensor so that they have effectively equal sensitivities after normalization. The preferred embodiment performs calibrations before each sample test or run, and optionally performs updates each tray cycle or after a predetermined number of tray cycles have occurred. The cleaning system can be used to clean the high-light-level calibration standard 102 on the tray during each tray cycle so that dust, debris, or grains on it are minimized in order to minimize calibration errors.

In the preferred embodiment, the tray moves forward at a constant and controlled speed. As the tray moves forward, feed mechanism 27 feeds grains in a controlled manner and at a substantially constant rate from the input grain hopper 26 onto the first stage top plate 47 of the vibratory conveyance mechanism 29. The grains are transported along the top plate 47 of the first-stage vibratory conveyance mechanism and tend to spread evenly and singulate in the troughs. The grains are conveyed to the end of this top plate 47 and fall onto the inclined surface of top plate 48 and off the end onto the underlying tray 31 that is in close proximity to this end of the top plate. As the tray travels forward, it is thereby loaded with grains in a controlled manner and the grains are substantially singulated in the troughs of the tray on the tray's top surface. The feed mechanism 27 and the vibratory conveyance mechanism 29 functioning is halted when the end of the tray 31 nears the end of the second-stage top plate 48 that feeds the tray. As the tray travels forward, the machine vision system acquires the data and the data is processed. When the tray reaches the end of its travel, the entire tray and the grains thereon have passed through the field of view of the light-sensing system 14. The end of the tray's travel is sensed and the direction of its travel is reversed. The tray moves in the reverse direction. The speed of the tray in the reverse direction can be significantly faster than in the forward direction, since video data is not acquired. Other embodiments may acquire the data in the reverse direction instead of the forward direction, and the speeds in the directions would be modified accordingly. In the preferred embodiment, as the tray starts in the reverse direction, the sweeper system 32 functions to position the fingers 56 into the troughs 30 to stop the grains' movement with the tray 31, and the grains are swept along the surface of the tray as the tray travels in the reverse direction. The grains are discharged through opening 57 from the tray through chute 33 into a collection hopper or container 34, or a means can be included to transfer these grains out of the apparatus in other embodiments. The tray continues to cycle, moving forward and then in reverse repeatedly along with the corresponding actions of the other components of the conveyance system as described, until all the grains in the sample have been processed and inspected. As this occurs, the data is processed in the preferred embodiment by all processing steps except determination of the final result and postprocessing, thereby minimizing the time to run a sample. After a predetermined time period has elapsed with no grains being detected, the tray cycling is terminated, the tray returns to its starting position, and the final results are computed and displayed, written to memory, and/or communicated to an external computer, terminal, apparatus, or system, or are stored. Postprocessing is then performed as commanded. The operator may remove the discharged grains from the collection hopper or container 34.

The operator could observe the displayed results, and/or can command the apparatus to store and/or transfer the data out of the apparatus. The data can be transferred to a computer to a printer, and/or to some form of data storage system internal or external to the apparatus. The data in an internal data storage device or system could be transferred out of the apparatus to another device or system. This data could then be further analyzed or processed or stored.

In the preferred embodiment, the operator may operate the apparatus directly, and/or may operate it via an external computer or computer terminal. The apparatus can have a port of some type (such as an RS-232 port in the preferred embodiment), or other communication means, to connect to and communicate with an external computer or terminal. Other embodiments may have either internal or external means for control. Furthermore, the operation of the apparatus may be accomplished by automatic means. The computer interface can be used to connect an automated process-control system to accomplish automated or semi-automated control and/or data collection. The apparatus may also be a partly- or fully-integrated part of a control system.

The operator may use an external computer or terminal to extract various other information. The preferred embodiment collects and can store various data that may be accessed by the operator and/or control system. Such information may be raw or processed data of the grains or other results. An example of such data is histograms of the particular measurements of the grains such as weight, area, length, and/or width. This data may be used in the control and/or optimization of the rice-milling or other process. This information may also be used for diagnostic purposes. Other information that may be acquired and/or assessed is the operational status and various other system information and parameters. In the preferred embodiment, the apparatus may be configured and functions performed by the operator from the computer or terminal, or by the process-control system. Other embodiments may have various ways to control it and to extract, store, communicate, and/or display data and results.

Thus, it is seen that the grain inspection and analyzer system of the invention provides an accurate, consistent, and automated means to measure broken content of grains and other agricultural products. It can be used for quality control, for grading, in the optimization of a processing plant such as a rice mill, and can be incorporated as a key element in an automated process-control system.

Although a specific grain feeding and presenting mechanism has been described, it will be apparent to one skilled in the art that the grains can be presented to the machine vision system in other ways. For example, the mechanism may use only one vibratory section or may use more than two stages. The troughs may not be used at all or may be used only on a tray or belt in alternate embodiments. A flat plate can be used as the vibratory feed plate, and it may have some characteristics or surface that is not completely flat, such as a pattern of raised areas or indentations that can help in singulation. Other embodiments may use inclined feeder plate(s), instead of the substantially horizontal orientation of the top surface of the top plates in the preferred embodiment. Other embodiments may use other types of mechanisms, which may or may not include vibratory means, to feed the grains onto the tray of other conveyance means. One embodiment may feed the grains directly onto a belt or tray or other grain-transport mechanism. In other embodiments, the belt or tray may be vibrating for all or part of the time it conveys grains. In the preferred embodiment, there are one or several troughs on the top of the tray 31 that substantially are in alignment with the corresponding troughs in the second-stage top plate of the vibratory mechanism. Their shape is such as to hold rice grains in a stable and consistent position during conveyance through the view of the camera. In the preferred embodiment, their shape is similar to the shape of the troughs in the top plate of the second vibratory feeder stage. Other embodiments may use different shapes on the tray and top plates. They may be designed for other grains or objects. Other embodiments may use other means to hold the grains in stable positions, or may have no particular means. One embodiment may have the camera view the grains in a stationary position, while another embodiment may have the grains conveyed slowly. Before and/or after viewing, the grains may be conveyed rapidly.

Other embodiments may employ air suction to hold the grains in place. Other embodiments may "freeze" the movement by using flash illumination and/or shuttering of the camera (such as electronic shuttering of video sensors/cameras). Yet another embodiment may have the data processing account for any movements of the grains that may occur while they are being viewed.

The machine vision system has been described with respect to a line-scan camera. It is apparent that other cameras can be used to view the grains and extract data such as a frame-scan or area-scan video camera. A specific grain-illumination system has been described. However, other means can be used to uniformly illuminate the grain.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

We claim:

1. A grain inspection apparatus for inspecting grain comprising:

a sensor means for sensing light from a plurality of contiguous spaces and providing an output signal for each of said contiguous spaces, a horizontally oriented grooved tray for supporting grains to be inspected in a plurality of side-by-side lines in said grooves, means for moving the grooved tray linearly in two opposite directions to sequentially present grains in said grooves to said contiguous spaces for sensing during movement in a first direction, means to illuminate the grains in the contiguous spaces, means for removing grains from said grooved tray when the tray moves in the secondary direction, and an electronic means configured to receive and process the output signals from said sensor and provide grain features signals representing one or more of length, width or area for grains in said contiguous spaces.

2. An apparatus as in claim 1 including computational means for receiving said grain feature signals and providing a signal representing broken-grain content in a sample.

3. An apparatus as in claim 2 means analyzing means for providing a signal representing the weight fraction or percentage of broken grain to the total sample weight.

4. An apparatus as in claim 1 wherein said sensor is a video camera.

5. An apparatus as in claim 4 wherein said video camera is a line-scan video camera.

6. An apparatus as in claim 1, including means for accepting and feeding said grain samples into the inspection apparatus, a grain conveyance means for conveying the grains from the said feeding means in a manner that singulates and conveys the grains to said grooved tray for loading onto said tray during movement of the tray in the first direction.

7. Apparatus as in claim 6, including computational means to estimate the weight of each grain viewed by said sensor in order to determine the weight of the broken grains in said sample of grains, the weight of the whole grains or the weight of the entire sample of grains, and whereby the said weight fraction of broken grains in the said sample of grains is computed from said weights of the broken and whole or total samples of grains.

8. An apparatus as in claim 2, wherein said computational means determines whether each grain from said grain sample is broken by comparing said grain feature signals to reference data.

9. An apparatus as in claim 2, wherein said computational means includes memory devices that are used as a look-up table that contains acceptable reference data, and said look-up table is used by said computational means in the determinations of whether the grains viewed by said sensor are broken.

10. An apparatus as in claim 6, wherein said grain conveyance means includes a vibratory mechanism that causes said grains to be transported and substantially separated from each other so they will not overlap each other when they are loaded onto said grooved tray.

11. An apparatus as in claim 6, wherein said tray includes calibration standards that travel into said contiguous spaces to be viewed by said sensor during movement of said tray whereby said sensor acquires calibration data, and a means is provided within the said electronic means to perform calibration and normalization of data subsequently sensed by said sensor and processed by the said electronic means.

12. An apparatus for inspecting grains as in claim 6, wherein said electronic means to acquire and process signals from said sensor includes computational means to estimate the weight of each grain viewed by said sensor in order to substantially determine the weight of the broken grains in said sample of grains, the weight of the whole grains or the weight of the entire said sample of grains, and to compute the said weight fraction of broken grains in the said sample of grains.

13. An apparatus for inspecting grains as in claim 6, wherein said electronic means to acquire and process signals from said sensor includes computational means to determine whether each grain from said grain sample is broken using predetermined data that is derived using an algorithm that is trained from grain data that is predetermined as to whether the grains are broken or not.

14. An apparatus for inspecting grains as in claim 13, wherein said computational means includes memory devices that are used as a look-up table that contains the said predetermined data, and said look-up table is used by said computational means in the determinations of whether the grains viewed by said sensor are broken.

15. An apparatus for inspecting grains as in claim 13, wherein said algorithm uses a technique selected from the group consisting of statistical pattern recognition techniques, neural network techniques, syntactic pattern recognition techniques, genetic techniques, fuzzy logic or fuzzy set techniques, adaptive recognition techniques, ad hoc techniques, and heuristic techniques.

16. An apparatus for inspecting grains as in claim 15, wherein said algorithm using a statistical pattern recognition technique that contains maximum-likelihood and probability-density estimation techniques.

* * * * *